(12) United States Patent
Caserta et al.

(10) Patent No.: US 7,095,953 B2
(45) Date of Patent: Aug. 22, 2006

(54) DISPOSABLE ELECTRICAL DEVICE FOR RELEASING ACTIVE SUBSTANCES

(75) Inventors: Andrea Caserta, Barcelona (ES); Julio Cesar Ruiz Ballesteros, Barcelona (ES); Cedric Morhain, Barcelona (ES)

(73) Assignee: Zobele Espana, S.A., Barcelona (ES)

( * ) Notice: Subject to any disclaimer, the term of this patent is extended or adjusted under 35 U.S.C. 154(b) by 0 days.

(21) Appl. No.: 11/136,307

(22) Filed: May 24, 2005

(65) Prior Publication Data

US 2005/0236384 A1 Oct. 27, 2005

Related U.S. Application Data

(63) Continuation of application No. PCT/ES02/00567, filed on Nov. 29, 2002.

(51) Int. Cl.
*F24F 3/14* (2006.01)

(52) U.S. Cl. ........................... 392/390; 392/385

(58) Field of Classification Search ................ 392/386, 392/390
See application file for complete search history.

(56) References Cited

U.S. PATENT DOCUMENTS

| 3,951,622 A | 4/1976 | Wilk |
| 4,157,787 A | 6/1979 | Schwartz |
| 4,161,283 A | 7/1979 | Hyman |
| 4,849,606 A | 7/1989 | Martens, III et al. |
| 5,518,790 A | 5/1996 | Huber et al. |
| 5,716,000 A | 2/1998 | Fox |

FOREIGN PATENT DOCUMENTS

| EP | 1 252 899 | 10/2002 |
| ES | 2 086 957 | 7/1996 |
| JP | 5-76583 | 3/1993 |
| WO | WO 84/02654 | 7/1984 |
| WO | WO 00/48460 | 8/2000 |
| WO | WO 01/68154 | 9/2001 |

OTHER PUBLICATIONS

International Search Report dated Mar. 10, 2003.
International Preliminary Examination Report dated Mar. 10, 2005.

*Primary Examiner*—Thor S. Campbell
(74) *Attorney, Agent, or Firm*—Katten Muchin Roseman LLP

(57) ABSTRACT

The device comprises a container (1) of active substance in liquid form, which is sealed by means of a permeable membrane (3) which lets the active substance vapour pass and prevents the passage of liquid, being completed with a porous support (5) on the inner face of the membrane (3), so as to take the active substance to the centre of the membrane (3), this being warmed by a heater element (9) with pins (10) which are coupled directly onto the pins (8) of a socket plug (7), via which the device is powered, so that the evaporation of the active substance takes place by warming and it issues to the exterior by ways of slots (12) provided in a housing (11) which joins the container (1) to the socket plug (7). The assembly forms a disposable device, although the container (1) can be embodied so that it is interchangeable.

12 Claims, 3 Drawing Sheets

DISPOSABLE ELECTRICAL DEVICE FOR RELEASING ACTIVE SUBSTANCES

CROSS-REFERENCE TO RELATED APPLICATION

This application is a continuation of International Application PCT/ES2002/00567 filed on Nov. 29, 2002, pending at the time of filing of this continuation application, the contents of which are herein wholly incorporated by reference.

OBJECT OF THE INVENTION

The present invention refers to a disposable electrical device for releasing active substances, which is of the type of those comprising a container of liquid (active substance), a heater element and a socket plug for the heater power supply.

The object of the invention is to supply a device of the aforesaid type which is designed to be used once, i.e. it is disposable, and wherein the fundamental basis of the innovations lies in the fact that the container includes a permeable diaphragm as the sealing base and external sealing by means of an impermeable film, which is removed at the start of use, with the special feature that the release and corresponding emanation to the atmosphere of the active substance takes place as a result of warming, i.e. above room temperature. The container may be interchangeable and used as a refill in a re-usable device.

BACKGROUND OF THE INVENTION

There are already known active substance electrical diffuser devices or appliances, wherein the active substance can be released in different ways, by means of heat, air flow, etc, and the appliance is re-usable.

Other electrical diffuser devices or appliances are also known that are made up of a single container with the active substance in liquid, gel or solid form (tablets, bottles with a wick, etc), where the container may be refilled or else be disposable. The devices composed of a bottle with a wick containing the active ingredient in liquid form are of particular interest, as they have the significant advantages of letting us know the remaining active ingredient capacity at all times and of being able to adjust the rate of release of active ingredient by means of the porosity of the wick. These devices, however, have the drawback of not assuring clean handling since active ingredient in liquid form may leak out in the event of incorrect handling.

Disposable appliances and devices are also known for diffusing active substances or principles, generally based on porous carriers impregnated with active substances, although appliances or devices of this type have the disadvantage of providing no control over the rate of release of the product or its consistency over time.

Finally, there is another type of appliance that consists of a receptacle for liquids with a "breathable" wall, i.e. it lets the vapours pass through but not the liquid, although its use on the market is confined to producing evaporation at room temperature.

In this respect, different documents may be cited each referring to patents, such as PCT 84/02654 or even U.S. Pat. No. 4,161,283, corresponding to volatile product dispenser devices, wherein evaporation takes place at room temperature and wherein membranes impermeable to the liquid but permeable to vapour are used so as to allow the vapour to escape to the exterior but not the liquid.

We may also cite U.S. Pat. Nos. 4,157,787, 3,951,622, 5,716,000 and 5,518,790, all referring to containers with one form and features or the other, but with a permeable membrane that allows the vapour of an active substance contained inside the bottle or container to pass, but always with the common denominator that evaporation takes place at room temperature.

Finally, U.S. Pat. No. 4,849,606 describes a container with a breathable membrane for use as a refill for an electrical diffuser, in this case, evaporation is achieved by means of warming the active ingredient. The drawback of this system is that the whole refill contents are warmed in the same way as if it were a tablet impregnated with active ingredient, so that the active ingredient may eventually be degraded, with the result that the efficiency of the evaporator device is impaired.

DESCRIPTION OF THE INVENTION

The device of the invention is designed to resolve the problems described above on the basis of a simple solution and structure and the introduction of innovations not used hitherto in the known devices intended for the evaporation of active substances.

More specifically, the device of the invention is based on producing the evaporation of the active substance by warming, comprising a container for the active substance in liquid state; a heater of special features; a socket plug for connection to the mains supply in order to energize the heater, and a housing between the plug body and the active substance container.

This heater may consist, for instance, of a metal oxide resistance, a ceramic wafer with PTC properties, or any other heater technology appropriate to the device.

Starting from these features, one of the improvements of the invention device consists of the fact that the container is designed to form a part of the device or else to be a replaceable element and to be used as a refill in re-usable devices.

In any case, the most novel feature of the device lies in the fact that the aforesaid container is sealed with a permeable membrane (breathable) taking the form of a film of one or more layers, of a polymeric nature, so as to allow the vapour produced by the warming of a part of the active substance to pass through, but preventing the liquid from doing so.

The object of the invention is, therefore, a container for use in an electric diffuser appliance, whether disposable or not, said container comprising a permeable membrane which seals its open base. This membrane is made of a polymeric material that allows the vapour of the active substance to pass through but does not allow the liquid to pass; with the special feature that the inner side of this face is provided with a plain porous support defining a wick by means of which the active substance is taken to the centre of the membrane.

Attached to the outer face of the permeable membrane there is an impermeable film, sealed on the actual container together with membrane, said impermeable film or foil defining a barrier which prevents the evaporation of the active substance during the storage of the container, this impermeable foil being removable before first use of the device.

Another novel feature is the inclusion of a plain porous support on the inner face of the aforesaid membrane, a support which will be embodied in high porosity paper (cellulose type, or in polymer or in any other porous material) with a configuration in the form of a disc, cross, etc, which enables the liquid or active substance with equal efficiency, in the four possible configurations or positions of the device, as in its use position, that is to say when fitted in a wall socket outlet, the membrane and the porous support are in the vertical position, so that by way of the special configuration the latter will take the liquid to the centre of the permeable membrane by means of capillarity, as the level of the liquid contained in the container will be below the level of the centre or mid-height of this membrane.

For its part, the plain porous support, as was said, forms a plain wick with two functions, in one case to permit the entry of a part of the liquid minimizing the risk that the principle or active substance may deteriorate with time, and the other function to supply the central part of the membrane with liquid, irrespective of the remaining capacity of this liquid and, above all, irrespective of the position in which the device is fitted in the mains socket outlet.

Another novel feature of the device is the inclusion of a film impermeable both to the liquid and to the vapour, situated in front of and attached to the active substance vapour passage membrane, a film which is provided to prevent vapour from escaping during storage and before the device is put to use, so that it has to be removed before being put into service for the first time.

The permeable membrane and this impermeable film are joined together by heat sealing, the aforesaid impermeable film being removable to allow the vapour to issue when the active substance is warmed.

For its part, the heater element includes pins by which it is pressed and at the same time it is attached to the plug socket, specifically to the pins of this plug, forming an assembly in which the heater is located outside the active substance container, although close to the membrane, matching up with an intermediate of the latter.

The direct connection of the heater to the socket plug saves connections, joints or wiring, and this means that no movement at all is between the heater element and the plug.

The device is completed with a housing that joins the active substance container to the plug-heater assembly, a housing that is provided with slots to allow the vapours generated by warming to issue.

Amongst the most significant advantages that may be mentioned stemming from the features of the device of the invention, are the following:

For the user:

Simple use, not requiring handling or installation.

It is an absolutely clean device as there is no leakage of liquid.

Plain indication of the end of use, since the amount of liquid in the container is clearly visible through it.

A device that works in all positions.

Long life, one device is sufficient for a season.

Being disposable, there is no possibility of getting the wrong refill.

There is no deterioration of the principle or active substance as the whole of the liquid is not subjected to warming action.

For the manufacturer:

It is not possible for third parties to copy the refill or replacement, as it is disposable, i.e. there is none.

Reduction of the number of parts making up the actual device.

Possibility of re-using the container in an electric diffuser, with minimal modifications, which could provide advantages both for the user and for the manufacturer, as it could be purchased separately as a refill or be used in disposable products.

DESCRIPTION OF THE DRAWINGS

To supplement the description being given and in order to assist clearer understanding of the features of the invention, in accordance with a preferred specimen practical embodiment of same, a set of drawings is attached as an integral part of said description, wherein the following is represented for illustrative and non-restrictive purposes.

PREFERRED EMBODIMENT OF THE INVENTION

Figure 1:
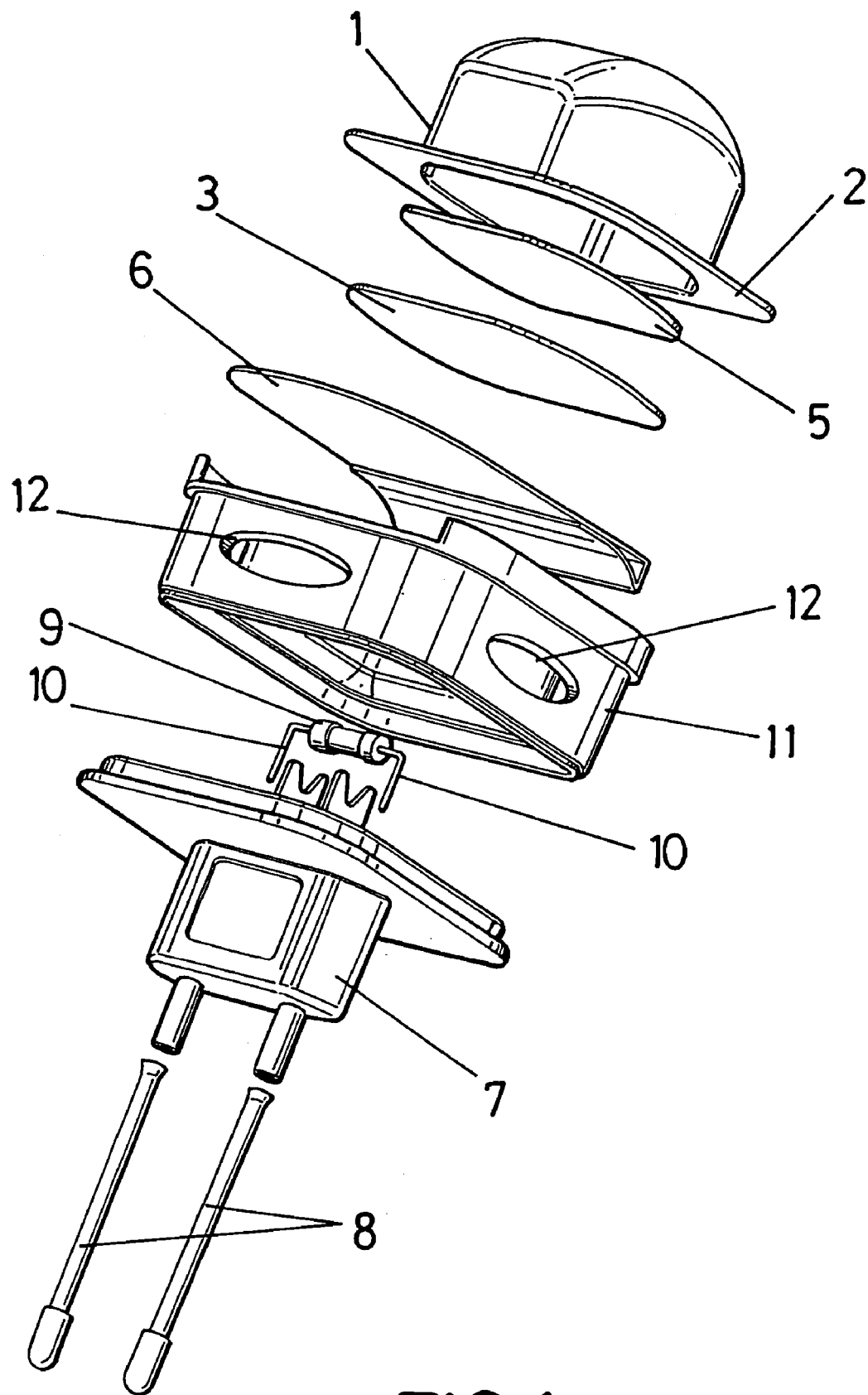
FIG. 1.—It shows a representation according to a general exploded perspective view of the different components or items making up the disposable electrical device for the release of active substances.
Figure 2:
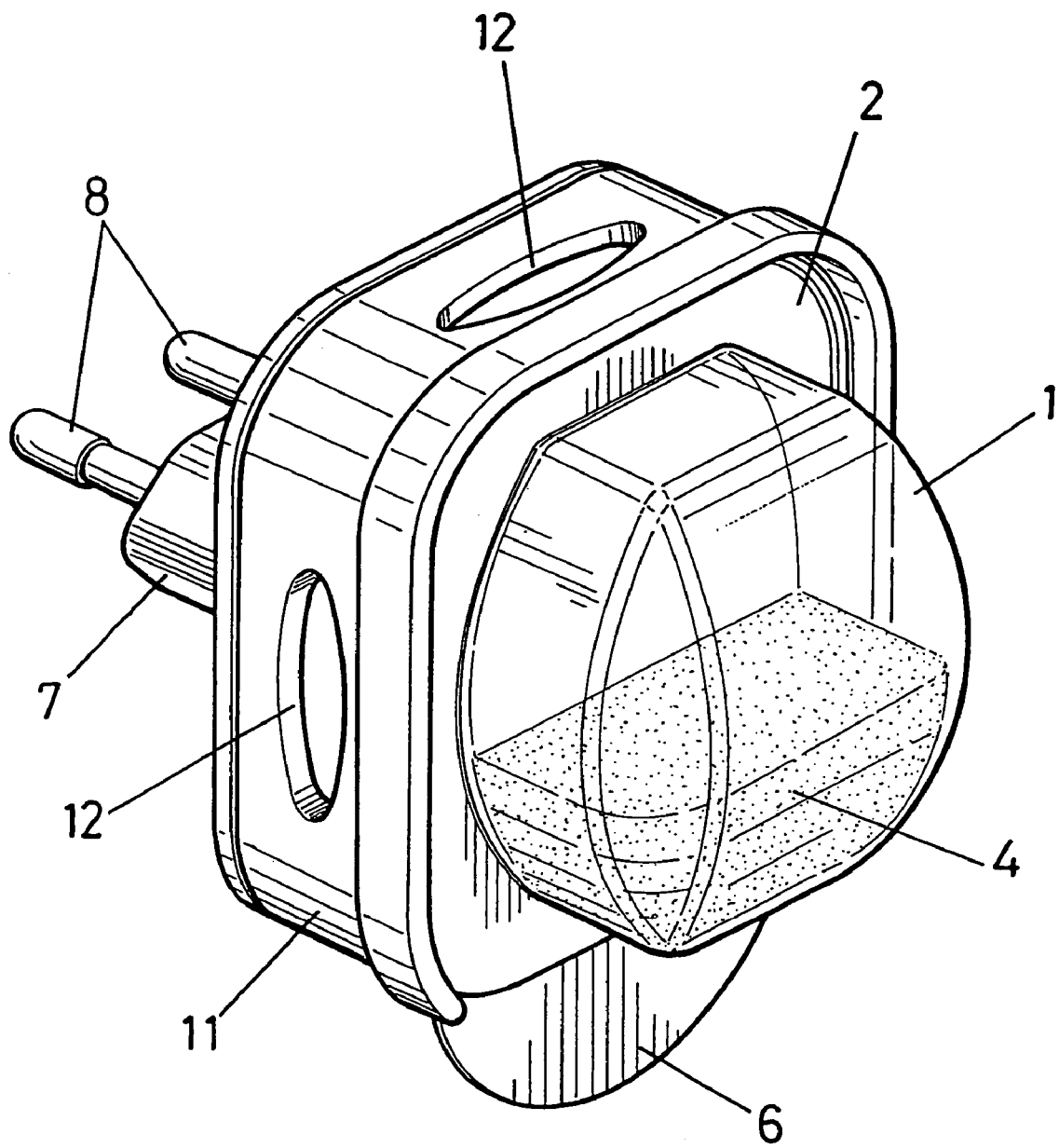
FIG. 2.—It shows a representation according to a general perspective of the device of the invention.

In the light of the above-mentioned figures it may be observed that the invention device comprises firstly a liquid container (1) with the active substance that is to be released, a container (1) which includes a perimeter wing (2) that matches up with its open base, which is sealed by means of a permeable membrane (3) whose characteristics are such that it allows the vapour of the principle or active substance to pass and prevents the issue of the liquid (4) contained. This membrane is composed of one or more layers, of a polymeric nature, for example, made from polyethylene, polypropylene, polyurethane or polyester amide, with a thickness of 15 to 150 micrometres.

The inner face of this permeable membrane (3) is provided with a foil (5) as a plain porous support element, which acts as a wick to convey the solution of active substance to the centre of the aforesaid membrane (3), being attached to the mouth of the container (1), specifically to the perimeter wing (2), by heat sealing.

This plain porous support (5) should be made of high porosity paper of the cellulose type, or polymer or any other porous material, of a suitable form to be equally efficient in the four possible arrangements of the device, while it may have a disc, cross, etc. configuration in order to be able to convey the liquid from the bottom of the container to the middle of the permeable membrane (3) in any of the positions, as was stated above.

In this way, the aforesaid porous support (5) fulfils two differentiated functions, in one case permitting only one part of the liquid to be warmed, so that there will be less risk of the active substance deteriorating with time, and furthermore it has the function of supplying the central part of this permeable membrane (3) with liquid, irrespective of the remaining amount of liquid and of the position in which the device is placed.

To prevent the vapour that might be generated during storage or handling from escaping, an impermeable film (6) a barrier for the afore-mentioned purpose is provided on the outer face of the permeable membrane, also attached to the perimeter wing (2) of the container (1), whose impermeable foil (6) should be removed before initial use of the device. It may be composed of one or more layers of metal and/or plastic foil with the above-mentioned properties, said layers being made for instance of aluminium, polyvinyl, ethylene-alcoholvinyl copolymer, etc.

Figure 3:
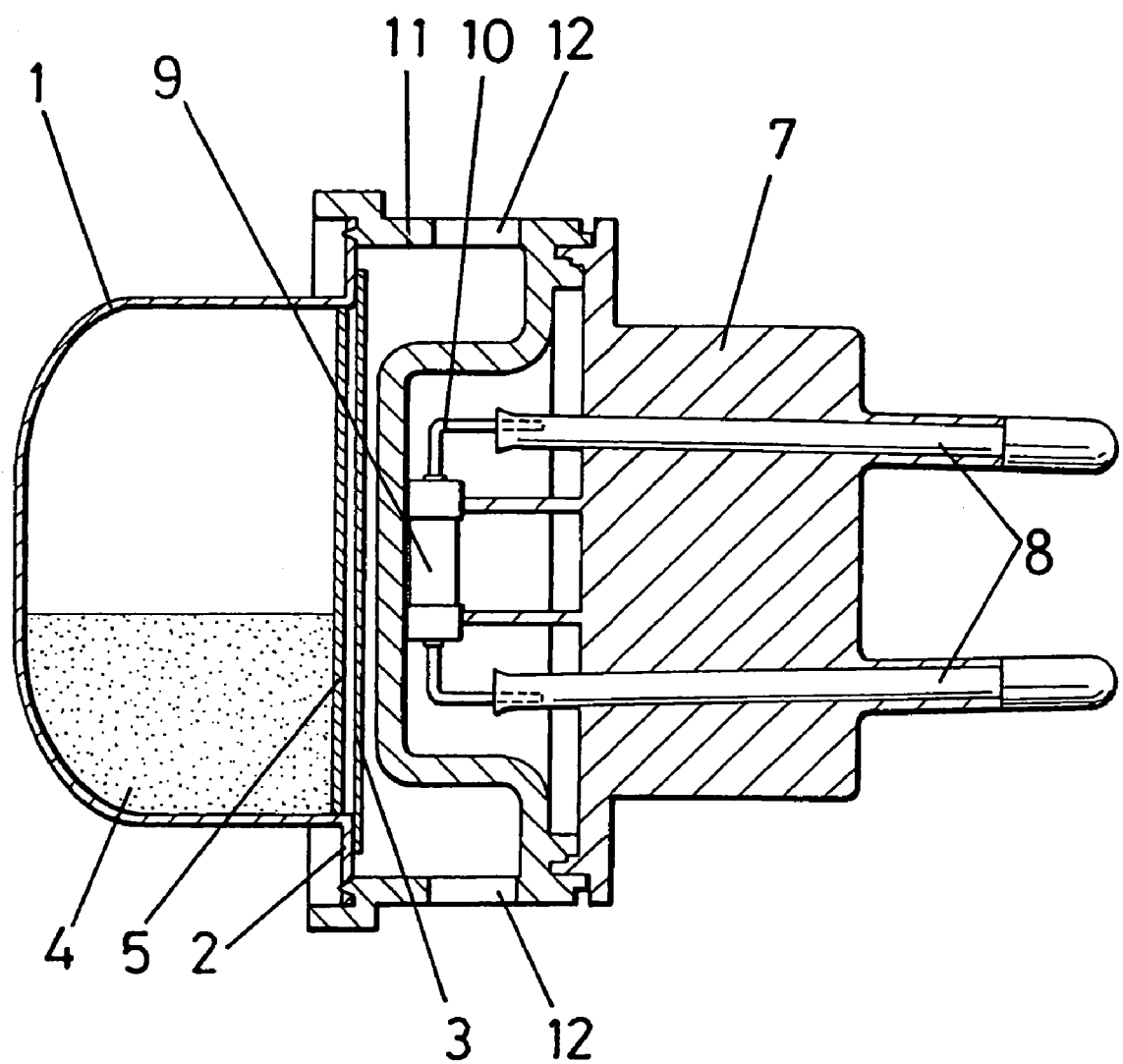
FIG. 3.—It finally shows a sectional view of the actual device, enabling the arrangement of the component parts to be seen clearly.

The device also comprises the respective plug (7) with the socket pins (8) for connecting up to a power pack or the mains for supplying the heater element (9) with which the device is provided, while it is also fitted with pins (10) connected directly to the pins (8) of the socket outlet (7), as is clearly shown in FIG. 3, forming a single unit.

The heater element (9) is located outside the container (1), a short distance from the permeable membrane (3), and at mid-height in relation to this, so that the manner of being installed or connected directly on the pins (8) of the socket (7) saves any kind of joint or wiring, as is the standard practice, so that no movement at all is required between the heater and the pins.

The device is completed with a housing (11) which secures the container (1) to the pin-heater assembly, a housing that is provided with slots or windows (12) through which the active substance vapours may issue to the exterior, i.e. to the atmosphere.

The device will function at an evaporation temperature above room temperature, as it should be pointed out that the device is designed both to bring about the evaporation of insecticides at a low temperature, which may range around 60° C., and to produce evaporation at higher temperatures.

The invention claimed is:

1. Electrical device for releasing active substances, which includes a container (1) for an active substance in a liquid state, a heater (9) for evaporating this active substance and a socket plug (7) for power supply to the heater, characterised in that the container (1) includes a permeable membrane (3) which seals an open base of said container, said membrane (3) being composed of a polymeric material which allows vapour of the active substance to pass through the membrane but prevents the active substance in liquid state from passing through the membrane, the inner face of said membrane (3) being provided with a plain porous support (5) defining a wick by way of which the active substance is taken to the centre of the membrane (3), whilst, externally to the membrane, in correspondence with an intermediate area of the membrane and adjacent to said membrane, lies the heater element (9).

2. Electrical device, as defined in claim 1, characterised in that attached to the outer face of the permeable membrane (3) an impermeable film (6) is provided, sealed on the actual container (1) together with the membrane (3), said impermeable film (6) defining a barrier that prevents the evaporation of the active substance while the container is in storage, said impermeable film (6) being removable before the device is first put into service.

3. Electrical device, as defined in claim 1, characterised in that it comprises an intermediate housing (11) between the container (1) and the assembly formed by the heater (9) and the socket outlet plug (7), said housing (11) being provided with slots (12) for the active substance vapour produced by warming to issue to the external atmosphere.

4. Electrical device, as defined in claim 1, characterised in that the plain porous support (5) has the form of a disc or cross, being embodied in paper of high porosity, hardness and strength or of polymer or any other porous material, whose configuration enables the liquid or active substance to be taken from the container (1) to the centre of the permeable membrane (3).

5. Electrical device, as defined in claim 1, characterised in that the heater element (9) is linked directly to the pins (8) of the socket outlet plug (7), forming a single unit with said socket outlet plug.

6. Electrical device, as defined in claim 1, characterized in that it is a disposable device.

7. Electrical device, as defined in claim 1, characterised in that it is designed to be re-used by means of replacing the container.

8. Container to be used in an electric diffuser device, whether disposable or not, said container being arranged for housing an active substance to be evaporated, the container (1) including a permeable membrane (3) that closes an open base of the container, said membrane (3) being composed of a polymeric material selected to let vapour of the active substance vapour pass through the membrane (3) and to prevent passage of the active substance in liquid state; the inner face of said membrane (3) being provided with a plain porous support (5) defining a wick by way of which the active substance is taken to the centre of the membrane (3); characterised in that the container is provided with means (2) for attaching the container to the electrical diffuser device for heating the active substance in the plain porous support.

9. Container according to claim 8, characterised in that the outer face of the permeable membrane (3) is provided with an impermeable film (6), sealed on the container (1) together with the membrane (3), said film (6) defining a barrier that prevents the evaporation of the active substance while the container is in storage, said impermeable film (6) being removable prior to initial use of the device.

10. Container according to claim 8, characterised in that the means (2) for attaching the container to the electrical diffuser device comprise a perimetric wing (2).

11. Container according to claim 8, characterised in that the means (2) for attaching the container to the electrical diffuser device are configured so as to arrange the container with the centre of the membrane (3) adjacent to a heater element of the electrical diffuser device.

12. A container assembly for an electric diffuser, the container assembly comprising:

a container for an active substance to be evaporated, the container comprising an open base;

a permeable membrane that closes the base of the membrane comprising a polymeric material, the membrane for passing the active substance in a vapor state and for retaining the active substance in a liquid state a plain porous support provided proximate to an inner face of the membrane and wicking the active substance to the membrane.

* * * * *